(12) United States Patent
Robertson (10) Patent No.: US 6,628,382 B2
(45) Date of Patent: Sep. 30, 2003

(54) LIQUID PHOTOMETER USING SURFACE TENSION TO CONTAIN SAMPLE

(76) Inventor: Charles William Robertson, P.O. Box 154, Rockland, DE (US) 19732

( * ) Notice: Subject to any disclaimer, the term of this patent is extended or adjusted under 35 U.S.C. 154(b) by 40 days.

(21) Appl. No.: 10/076,706

(22) Filed: Feb. 15, 2002

(65) Prior Publication Data

US 2002/0154299 A1 Oct. 24, 2002

Related U.S. Application Data

(63) Continuation of application No. PCT/US00/22532, filed on Aug. 17, 2000.
(60) Provisional application No. 60/150,066, filed on Aug. 20, 1999.

(51) Int. Cl.$^7$ .................................. G01N 21/01
(52) U.S. Cl. ........................ 356/246; 356/440
(58) Field of Search ................ 356/246, 440, 356/436

(56) References Cited

U.S. PATENT DOCUMENTS 4,286,881 A * 9/1981 Janzen ................. 356/440
4,643,580 A 2/1987 Gross et al.
4,910,402 A 3/1990 McMillan
5,739,432 A 4/1998 Sinha
5,926,262 A 7/1999 Jung et al.

FOREIGN PATENT DOCUMENTS

WO   WO01/14855 A1   3/2001

OTHER PUBLICATIONS

"Laboratory Equipment", 1998, World Precision Instruments, Sarasota, FL, pp 114–115, 117–118.
"Cuvette Holders for I–cm Cuvettes", Ocean Optics June 29, 1999, Dunedin, FL.

* cited by examiner

Primary Examiner—Richard A. Rosenberger
(74) Attorney, Agent, or Firm—Edward J. Kaliski (57) ABSTRACT

Method and apparatus of spectrophotometry or the like on extremely small liquid samples in which a drop is held between two opposing surfaces by surface tension and one surface is controllably moved toward and away from the other. To provide and transmit exciting energy through the drop for measurement, the optical fibers go through a surface and are finished flush with its surface. One of the surfaces can be swung clear of the other for easy cleaning between tests.

30 Claims, 9 Drawing Sheets

FIG. 9

LIQUID PHOTOMETER USING SURFACE TENSION TO CONTAIN SAMPLE

FIELD OF INVENTION

This invention relates to the fields of photometry, spectrophotometry, fluorometry, spectrofluorometry and the like and their use in optically quantitating and or characterizing liquids and solutions.

BACKGROUND OF INVENTION

This invention relates to the field of spectrophotometers and related instruments. More particularly the invention relates to ultra low volume instruments working in the volume range of 2 microliters or less. Such devices are particularly useful in quantitation of biotechnology samples including nucleic acids or proteins where it is desirable to keep sample loss and/or cross-contamination to a minimum.

The prior art contains examples of attempts to supply low volume spectrophotometers. World Precision Instruments of Sarasota, Fla. offers parts from which an instrument handling less than 20 microliters can be built for around $3000. This uses a fiber optic dipping probe with a tip diameter of 1.5 mm (DipTip®), their miniature fiber optic spectrometer and F-O-Lite H light source. With a deuterium lights source (D2Lux) a UV spectrophotometer can be constructed.

U.S. Pat. No. 4,643,580 to Gross et al. discloses a photometer head in which there is a housing for receiving and supporting small test volumes. A fiber optic transmitter and receiver are spaced within the housing so that a drop can be suspended between the two ends.

McMillan, in U.S. Pat. No. 4,910,402, discloses apparatus in which a syringe drops liquid into the gap between two fixed fibers and an IR pulse from a LED laser is fed through the droplet. The output signal is analyzed as a function of the interaction of the radiation with the liquid of the drop.

Ocean Optics, of Dunedin, Fla. 34698 supplies a SpectroPipetter for microliter-volume samples using a sample volume of about 2 microliters. The optics not only carry light to and from the samples but act as a plunger to load the sample. The tip of the pipette includes the sample cell.

Liquids, mixtures, solutions and reacting mixtures are often characterized using optical techniques such as photometry, spectrophotometry, fluorometry, or spectrofluorometry. In order to characterize samples of these liquids, the liquid is usually contained in a vessel referred to as a cell or cuvette two or more of whose sides are of optical quality and permit the passage of those wavelengths needed to characterize the liquid contained therein. When dealing with very small sample volumes of say from 1 to 2 microliters, it is difficult to create cells or cuvettes small enough to to be filled and permit the industry standard 1 cm optical path to be used. It is also difficult and/or time consuming to clean these cells or cuvettes for use with another sample. In the case of photometry or spectrophotometry, the value most commonly sought is the sample absorbance A defined by $$A = -\log T$$

Where T is the transmittance, or $$A = \log(I/I_0)$$

where $I_0$ is the level of light transmitted through a blank sample (one containing all components except the one being measured or one whose absorbance is known to be negligible and with optical properties identical to those of the sample being measured), and I the level of light transmitted through the sample being measured. Most commonly the absorbance value is measured in a cell or cuvette with a 1 cm path length. However, Lambert's Law states that for a collimated (all rays approximately parallel) beam of light passing through a homogeneous solution of uniform concentration the absorbance is proportional to the path length through the solution. For two path lengths X and Y, (Absorbance $x$)/(Absorbance $y$)=(Pathlength $x$)/(Pathllength $y$)

Thus it is reasonable that absorbance can be measured with path lengths other than 1 cm and corrected for path length to the equivalent value for a 1 cm path which can be more easily compared to data from other spectrophotometers. The sample path lengths in the range of 0.2 to 2 mm used in this invention can be used to generate absorbance values that can be easily corrected to the 1 cm path equivalent.

Although liquids confined by surface tension and an optical surface are well known, e.g. raindrops on the window, establishing a collimated optical light path of known length through such confined liquids has been perceived as difficult. The recent advent of small spectrometers designed to be used with fiber optics has made it possible to consider spectrophotometric geometries not readily possible before.

It is the object of the instant invention to make use of the surface tension of a microliter or submicroliter sample of liquid to provide suficient means to confine it within the analysis region of an optical analysis instrument and to carry out the requisite measurement.

STATEMENT OF INVENTION

The invention is an optical instrument for photometric, spectrophotometric, fluorometric or spectrofluorometric analysis of liquids contained between two substantially parallel surfaces on anvils spaced apart a known distance, wherein the sample liquid is confined by the surfaces and the surface tension of the liquid. Each of these surfaces contain an optical fiber mounted coaxially with each and perpendicular to the parallel confining surfaces The shape and nature of the surfaces serve to confine the liquid so as to center the confined droplet in the optical path of the optical fibers embedded in the surfaces. An apparatus supporting the surfaces permits the surfaces to be controllably separated to allow loading of the sample and cleaning of the surfaces after sample analysis.

For some applications, the optical fibers can be replaced by miniature sources like light emitting diodes (LEDs) and detectors or detectors with optical filters. The LEDs with their characteristically small emitting area would replace the source fiber and small solid state detectors with associated filters like those used in color charge coupled devices (CCDs) for imaging would replace the receiving fiber and spectrometer.

DESCRIPTION OF THE INVENTION

Figure 1:
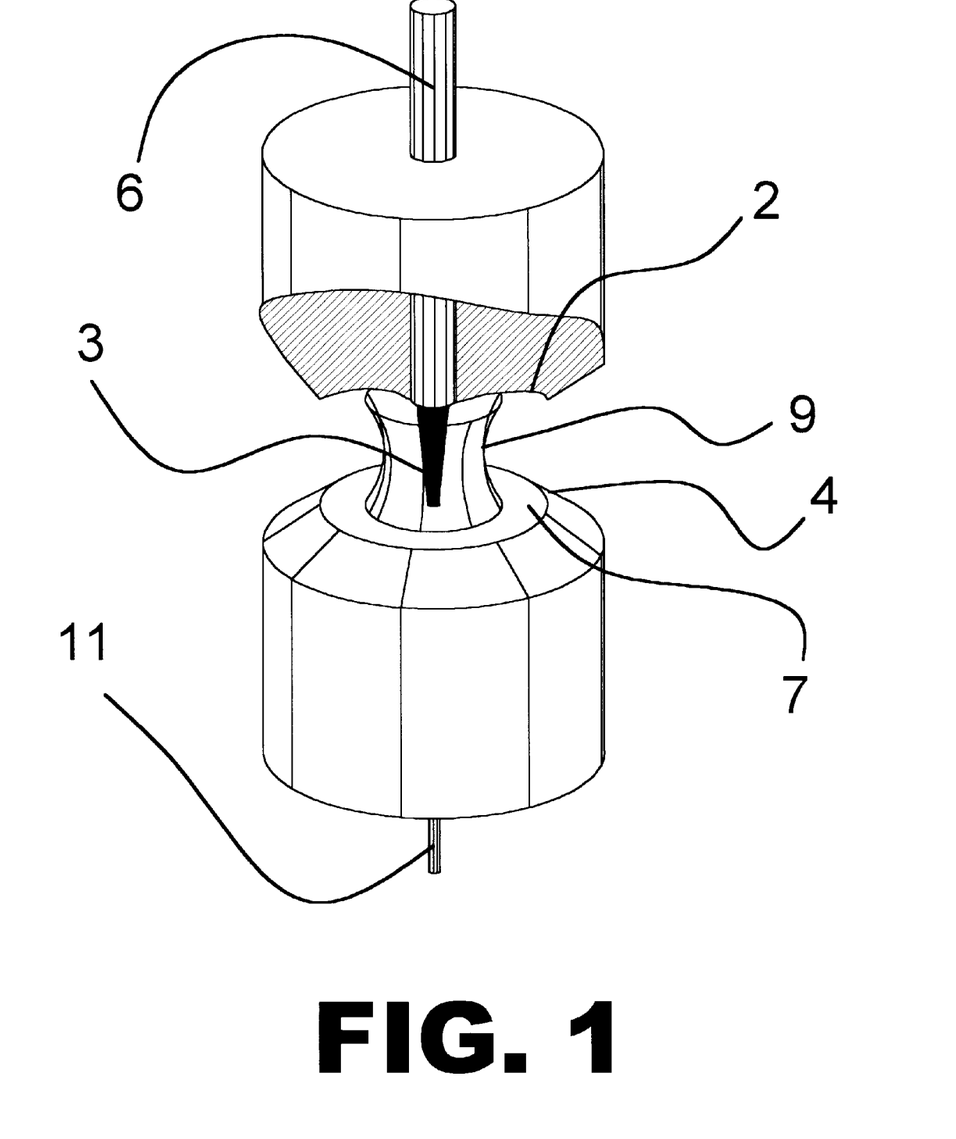
FIG. 1 is a drawing of a cutaway section of the optical path of the invention.

The liquid sample shown in FIG. 1 is contained by its surface tension between surfaces 2 and 7 also shown in FIG. 1. Light 3 from the system source coming through the fiber contained in and flush with surface 7 radiates upward through the liquid sample and is collected by the larger fiber or light pipe 6 in the upper surface 2 and sent on to the analysis photometer or spectrometer for absorbance measurements. For making fluorescence measurements, the excitation light can also be brought to the sample through fibers surrounding the collection fiber 6 as is shown in 83, FIG. 2, This reduces the need for high excitation wavelength rejection on the part of the spectrometer collecting the fluorescence light from the sample through collection fiber 6.

Figure 3A:
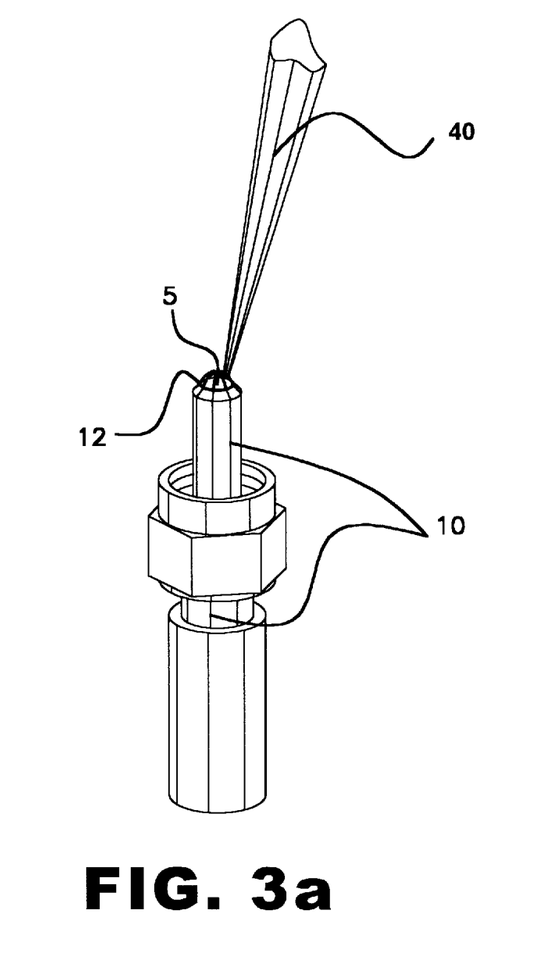
FIG. 3a is a perspective drawing of a process by which the sample is loaded into the optical path of the invention.

Samples are loaded onto the lower source with a pipetting means 40, FIG. 3a such as a 2 microliter Pipetteman® from the Ranin® Corporation of Woburn, Mass., part of the tip of which is shown in 40. The droplet 5 when emptied from the pipette, if of sufficient volume, will spread to cover the lower anvil surface 7, FIG. 1 which is typically the end of an industry standard SMA fiber optic connector 10, FIG. 3a (found as connectors on the ends of optical patch cords like p/n P-400-2-UV-VIS from Ocean Optics inc. of Dunedin, Fla.) until it encounters the sharp edge shown as 4, FIG. 1. For most SMA connectors the approximate 2 mm end diameter can be effectively covered with 2 microliters of water or a water-based solutions.

Figure 3B:
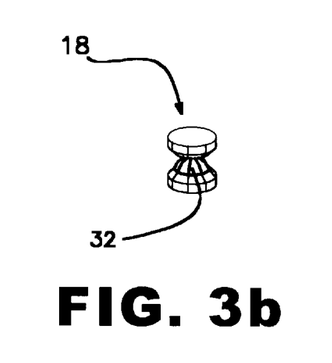
FIG. 3b shows the sample between the two anvils in the measurement position.
Figure 3C:
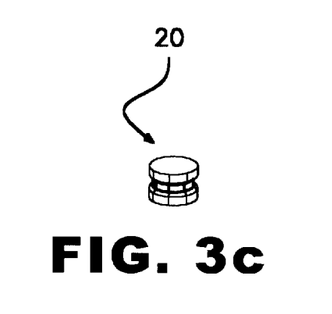
FIG. 3c shows the sample compressed between the two anvils in the short path or sample compression position.
Figure 3D:
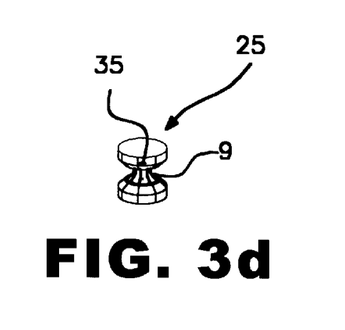
FIG. 3d shows the sample column drawn by opening the anvils from the sample compression position to the sample measurement position.

The upper second surface is brought into the measurement position 18, FIG. 3b and then into close proximity 20 to the lower surface 7, FIG. 3c, making contact with the deposited droplet wetting the entire confining surface before returning to the sample measurement position and drawing up the sample measurement column 30, FIG. 3d shown in 25. By applying blank samples, samples missing the component being analyzed, the difference in transmitted light intensity can be used to characterize the sample according to $$A = -\log(I/I_0)$$

where $I_0$ is level of transmitted light with the component being analyzed absent, and I is the level of light transmitted through the sample and A is the absorbance value which can be related to the concentration of the component being analyzed by Beer's law which states that for solutions 1 and 2 that $$\frac{(\text{Absorbance 1})}{(\text{Absorbance 2})} = \frac{(\text{Concentration 1})}{(\text{Concentration 2})}$$

Thus, when compared with a blank sample, the concentration can be directly determined from the absorbance A.

Figures 4A, 4B:
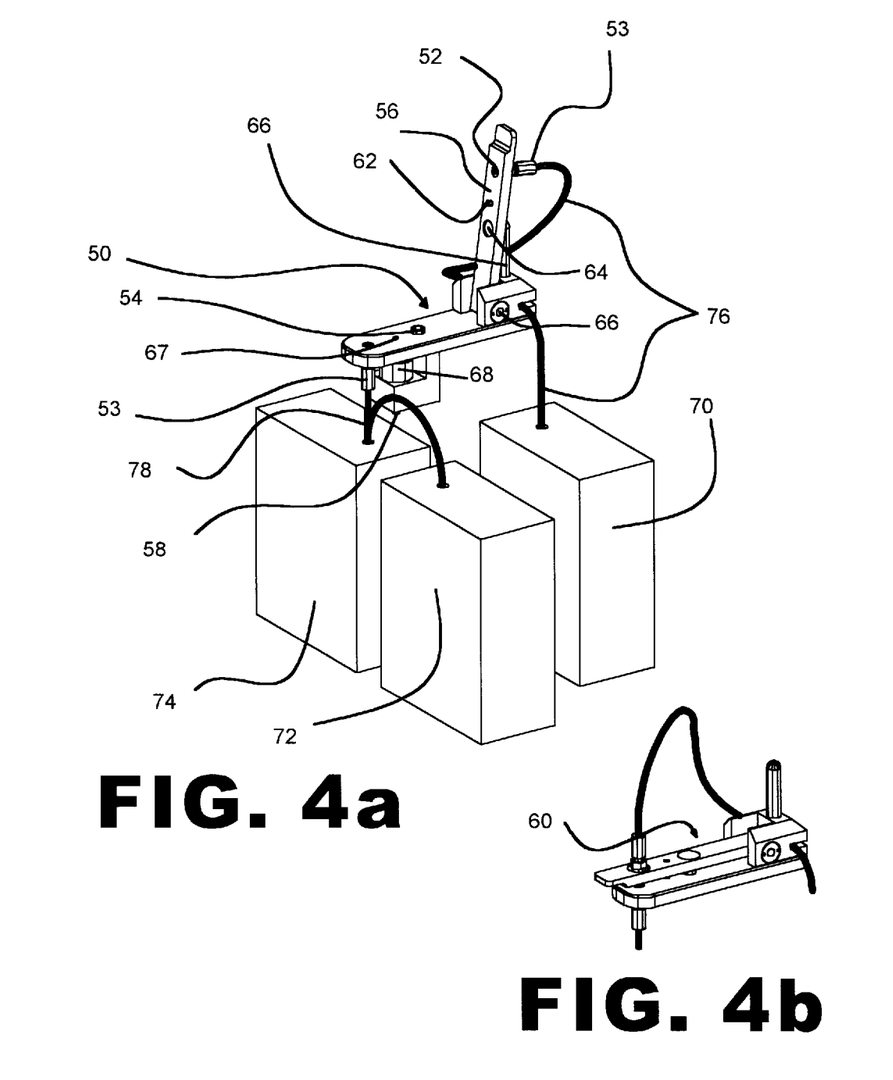
FIG. 4a is a perspective drawing of apparatus of the invention in its open position with the source and spectrometers.
FIG. 4b shows the apparatus in its closed position as it would be for sample compression or analysis.

The SMA optical fiber connectors can be held in place by apparatus shown in FIGS. 4a and 4b. The light from the system source 74 (Ocean Optics inc. p/n DT-1000, a combined deuterium arc and quartz halogen incandescent lamp, alternatively a xenon flashlamp can be used) is coupled through a bifurcated optical fiber assembly (Ocean Optics inc. p/n BIF-100-2-UV-VIS) to the apparatus 50 with the second fiber of the bifurcated assembly going to reference slave spectrometer 72 (Ocean Optics p/n SD2000). The SMA connectors 53 are mounted to the apparatus by means of threaded couplers 52 (World Precision Instruments p/n 13370) which are threaded into the apparatus. The swing arm 56 carrying the upper optical fiber 53 can be lowered to align the source with the detection fiber as is shown in 60, FIG. 4b. The swing arm spacing is controlled by pin 62 resting on the plunger 67 of solenoid 68 (Lucas Ledex of Vandalia, Ohio p/n 174534-033) shown mounted below the apparatus. The other end of the solenoid plunger 67 rests on spring plunger 58 (Manhattan Supply of Plainview, N.Y. p/n 82412032). The sample can be compressed as is shown in 20, FIG. 3c by pushing on the swing arm 56 so as to push the solenoid plunger to the limit of its travel or by actuating the solenoid electrically and pulling the plunger to its stop. The swing arm is held in both its up and its down position by magnet 64 (Edmund Scientific of Barrington, N.J. p/n J35-105) attracted to either post 66 or allen head cap screw 54. With the swing arm in its raised position, the sample detection surfaces may be cleaned by wiping the sample from both the lower and upper SMA connector ends before reloading.

Figure 6A:
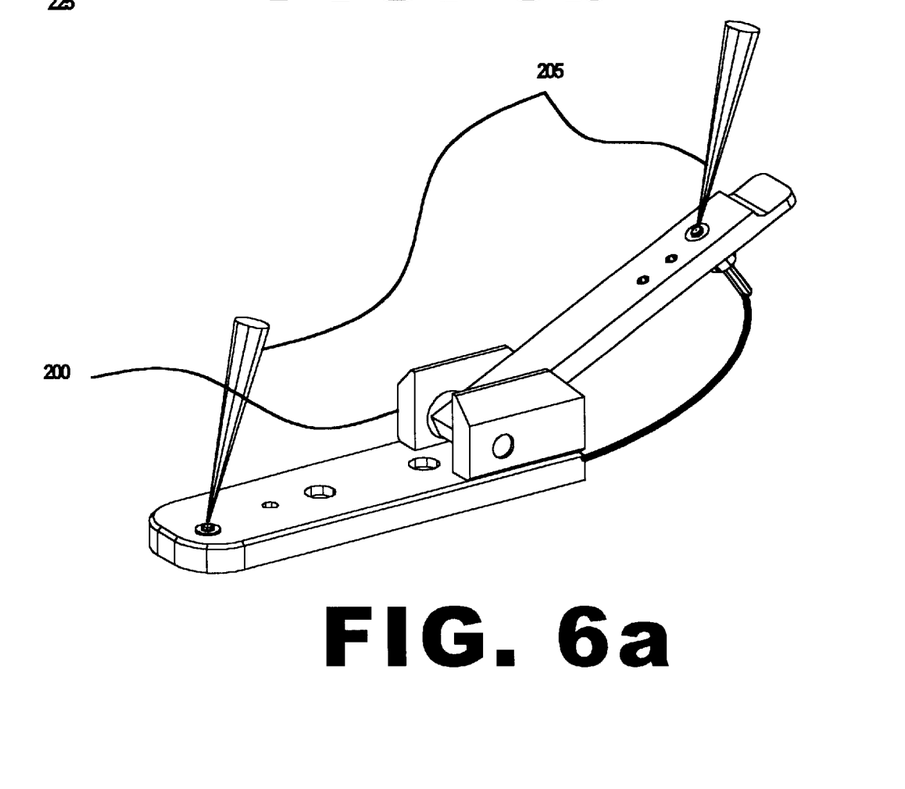
FIG. 6a is a perspective view of the open instrument of the invention showing two pipetter tips loading two parts of a mixture each on either side of the measurement apparatus.

Light transmitted through the sample is collected by the upper fiber and coupled to the detection master spectrometer 70 (Ocean Optics p/n SD2000). The fiber is confined to minimize flexure of the fiber which would cause unnecessary variability in its transmission and thus unnecessary variation in measured absorbances. The swing arm is precision pivoted on a shaft turning in two preloaded ball bearings 66. Note that the instrument is opened by turning through an arc sufficient to permit loading and cleaning. See FIG. 4. Preferably it is opened at least 90 degrees as seen in FIG. 4 and more preferably the arc approaches 160 degrees as seen in FIG. 6a.

Figure 2:
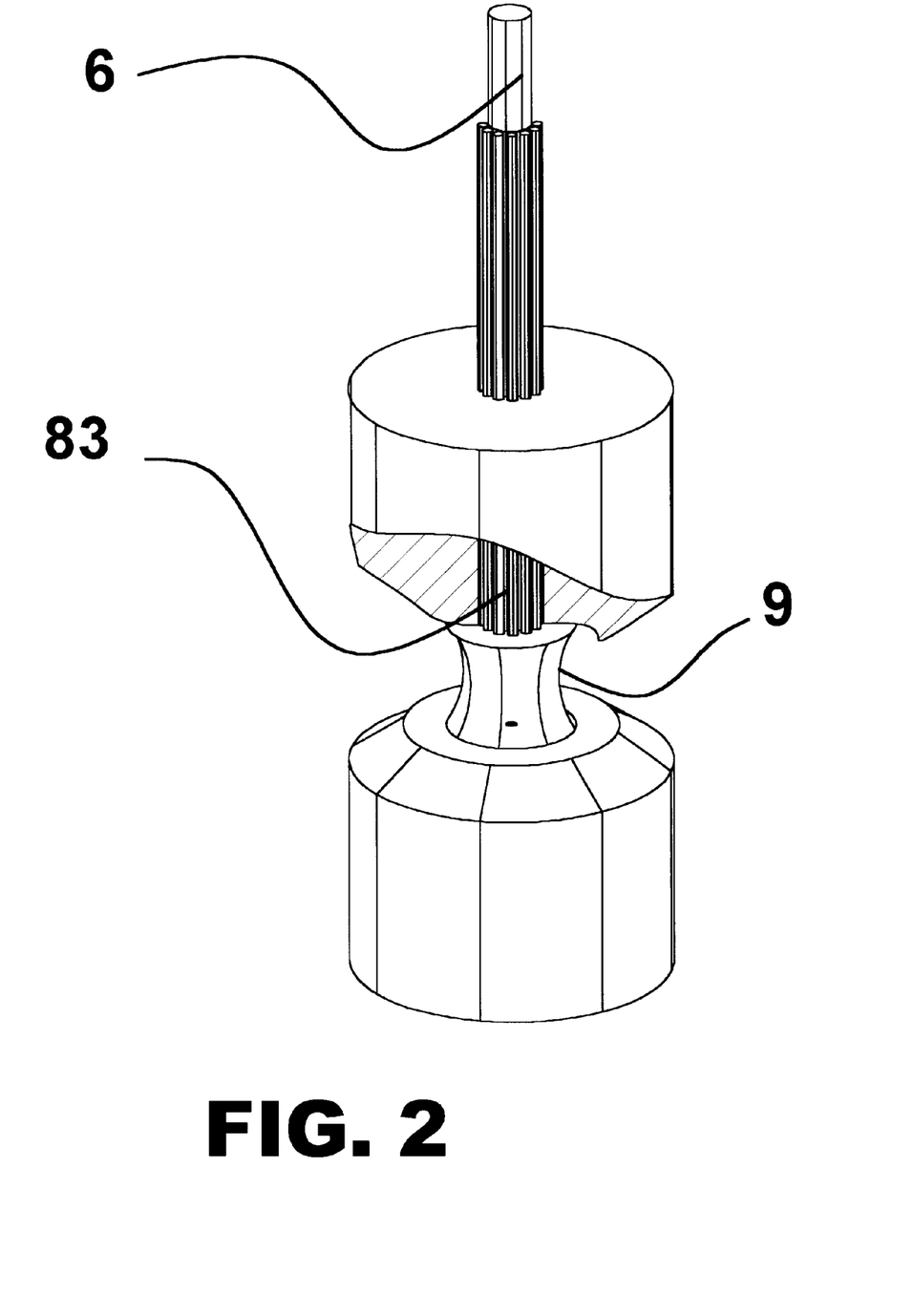
FIG. 2 is a drawing of a cutaway section of the optical path of the invention with additional fluorometric source optical fibers shown.

In order to accomplish illumination of the sample for fluorescence as shown in 83, FIG. 2, the upper fiber assembly would need to be custom made so as to surround the collection fiber with illumination fibers. These would be bundled and illuminated with the source wavelength compatible for use with the sample.

Figure 5A:
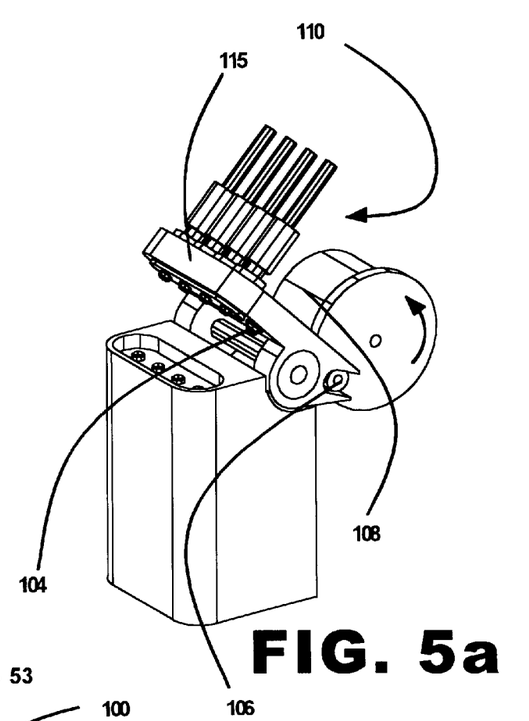
FIGS. 5a and 5b show a system with four spectrophotometer systems operating simultaneously for use on robotic platforms in both the loading, 5a, and measuring, 5b, configurations respectively.
Figure 5B:
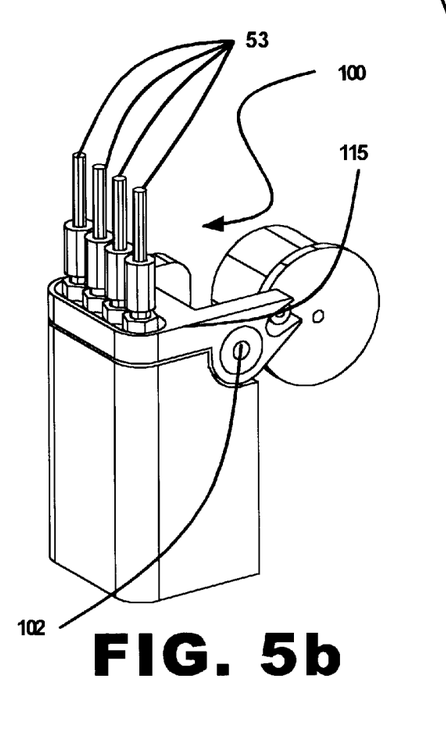

As seen in FIGS. 5a and 5b, two or more of the photometric systems can be grouped in unitary form to test multiple samples simultaneously. Such a multiple parallel photometer system can be employed with a multi-pipette robot system such as the MultiPROBE II made by Packard Instrument Company of Meriden, Conn. In FIG. 5, the four signal fibers 6, FIG. 1 each feed a fiber optic spectrometer and the spectra are taken simultaneously. The four source fibers, not shown, are illuminated from a single source which may be referenced with a single reference spectrometer as with the single channel system. In FIG. 5 the apparatus is shown closed 100 and open for loading 110. Opening and closing are controlled by a rotary actuator 108 such as p/n 195191-031 made by Lucas Ledex of Vandalia, Ohio and cam 106. Spring plunger 104 such as p/n 3408A35 sold by McMaster-Carr of New Brunswick, N.J. controls the position and provides the spring force against which the compression overtravel is accomplished for initial spreading of the sample.

Figure 6B:
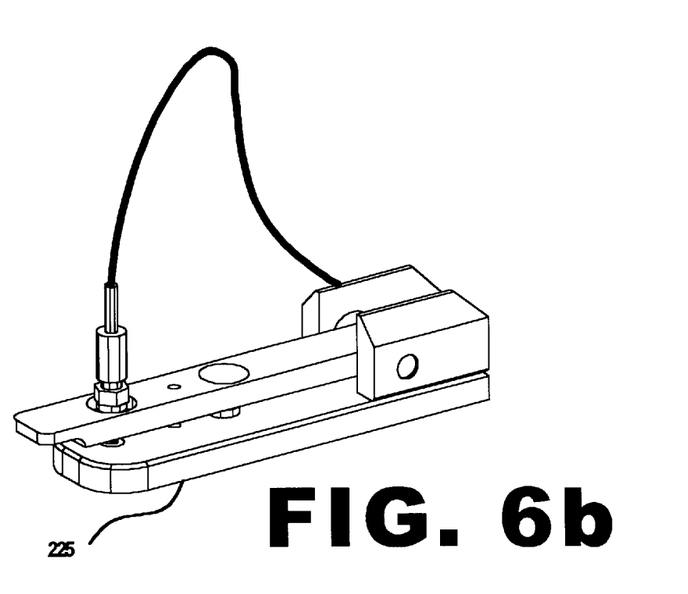
FIG. 6b shows the instrument of FIG. 6a closed.

Samples for photometric analysis can also be loaded into the sample handling apparatus in two parts, one on each of the opposing surfaces. This is especially useful where the sample of interest is a two part reacting mixture where the one or more of the beginning absorbance, the ending absorbance, and the rate of reaction are of interest and can be measured photometrically of fluorometrically. Samples of this sort can be loaded into the open spectrophotometer as shown in FIG. 6a, where two pipetter tips 205 are shown loading the two parts of the mixture, each on either side of the measurement apparatus 200. When closed as shown in FIG. 6b, measurement can be made from onset of any reaction. The exact time of sample mixing can be determined from photometric or fluorometric measurement through the apparatus optical fibers.

Figure 7A:
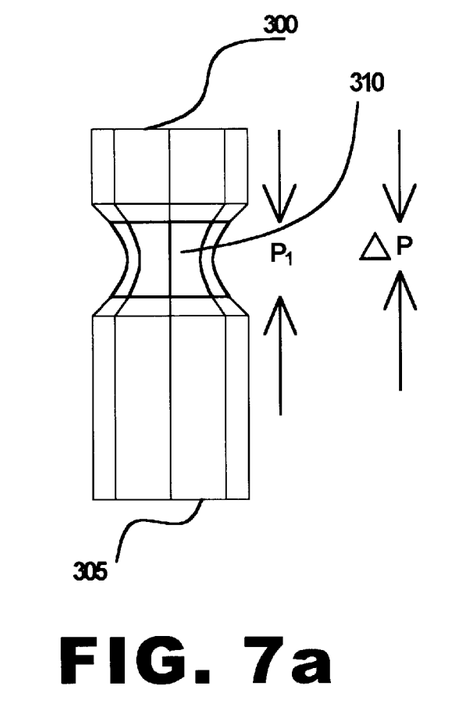
FIGS. 7a and 7b show perspective views of two path lengths provided by the apparatus of the invention so that a differential absorbance path is established.
Figure 7B:
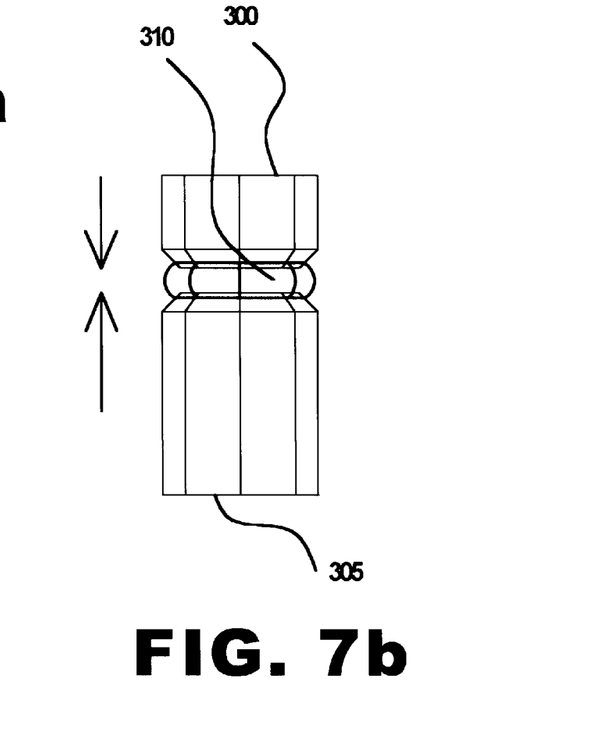

Samples can also be measured with a differential absorbance path as shown in FIGS. 7a and 7b. Here sample absorbance can be measured by changing the optical path over which the absorbance is measured, measuring the sample at each of one or more path lengths, where the difference in path length combined with the difference in transmitted intensity can be used to calculate the sample absorbance. This can be of significant value if the sample is highly absorbing and the accuracy of the path difference for a small path difference can be better determined than the absolute full optical path. Measurements are taken as shown in FIG. 7a, where sample 310 is shown with a relatively long path $P_1$ and FIG. 7b with a relatively short path length $P_2$ between the moveable anvils carrying the facing surfaces with one or more path differences $\Delta P$ with the absorbance at the shorter path $P_2$ being subtracted from the absorbance of one or more of the longer paths to arrive at the absorbance of the sample.

Figure 8:
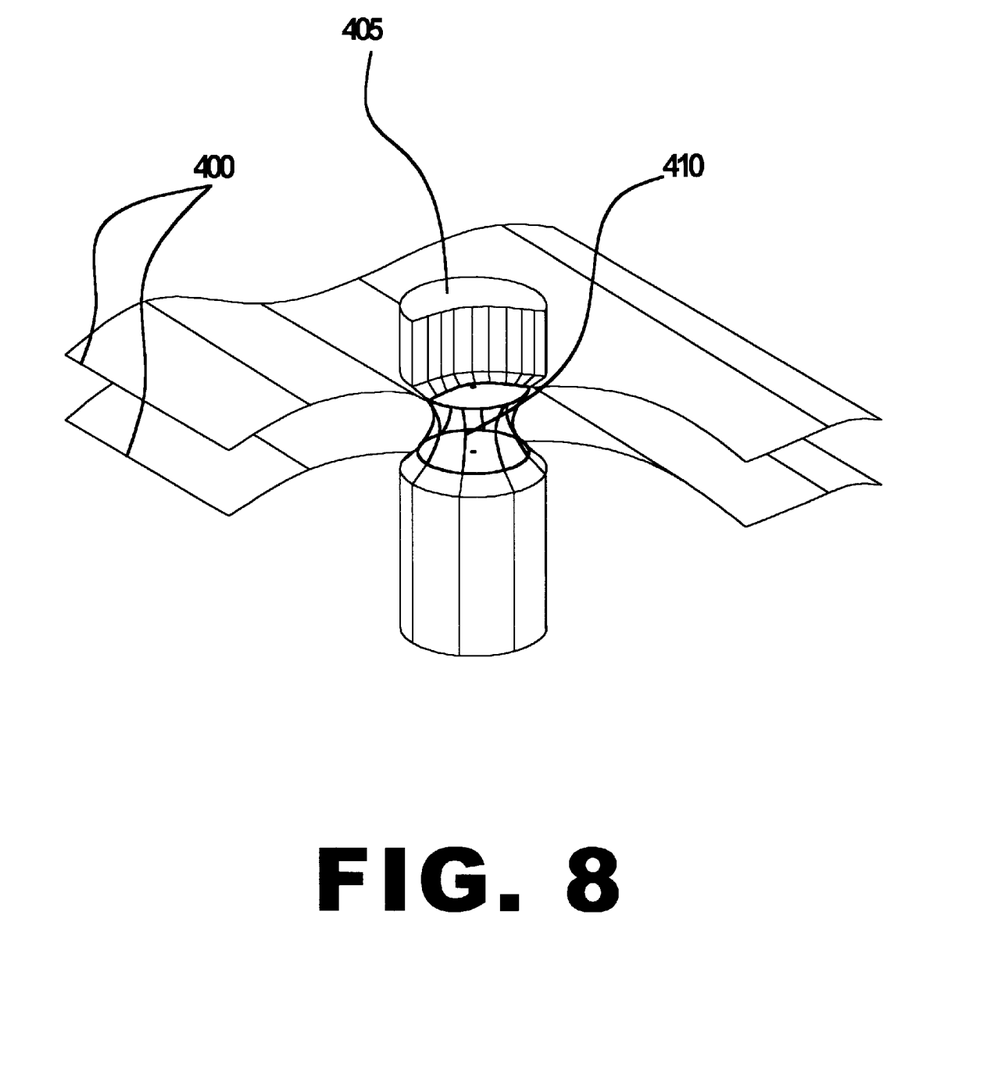
FIG. 8 shows a perspective view of a measurement made in the instrument of the invention holding the sample between two transparent sheets.
Figure 9:
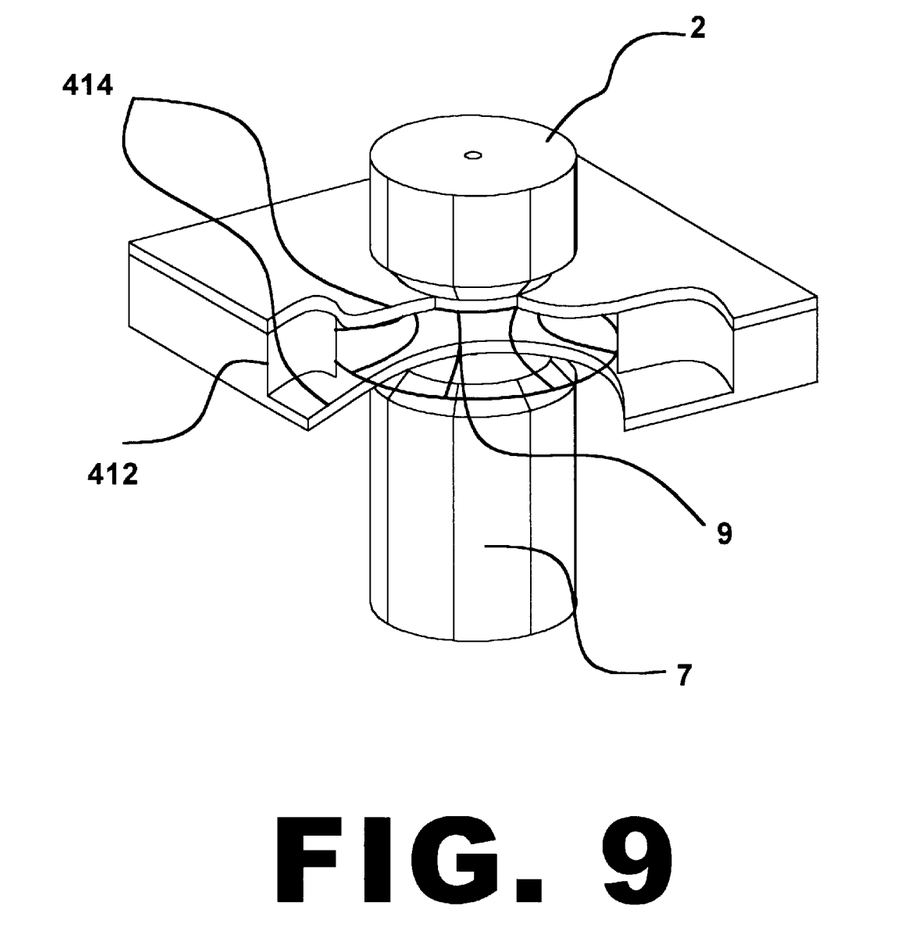
FIG. 9 shows a perspective view of a measurement made in the instrument of the invention holding the sample within a transparent container with flexible walls.

Samples can also be contained between two thin sheets of optically transparent material like Teflon™ or polyethylene films. As shown in FIG. 8, the same sort of column drawn between the two parts of the sample apparatus can be drawn between the two thin optical sheets 400 where the anvils of the apparatus are wetted to the film surfaces to minimize reflection at the interface and aid in pulling the measurement column. This would be of significant use where samples are corrosive or dangerous to handle for safety reasons and containment of the sample is preferred. The two containing sheets 400 allow the two parts 2 and 7 of the sample apparatus to draw the sample 9 into column 410. Differential measurement of the sort discussed above would be of significant value in this sort of measurement as the effects of the interfaces could be minimized with differential measurement. The two sheets 400 can be replaced by a small vessel 412, see FIG. 9, with flexible walls 414 such that the sample contained can be pulled into a measurement column. The column is pulled by pushing the anvils of the apparatus into the film until contact is made by both films, then drawing the measurement column. The compliance of the film will cause it to remain in contact with the anvils. Wetting the anvils before making contact will assist in maintaining contact and in minimizing reflection at the interface between the film and the optical fiber imbedded in the anvil. Once the measurement column is pulled, absorbance can be measured as a difference in absorbance between two path lengths.

What is claimed is:

1. A photometric or spectrophotometric apparatus wherein a sample in the form of a liquid drop is contained by surface tension forces between two planar surfaces, one containing a photometric or spectrophotometric source and the other a photometric or spectrophotometric detector and an optical path is established through the sample between the two surfaces said apparatus comprising:

first and second anvil surfaces at least one being moveable relative the other to any one of three positions:
an adjustable sample loading position so selected that the at least one moveable surface and the other surface are so remotely spaced that a liquid drop can be placed on the first surface;
an adjustable sample compression position so selected that the surfaces are opposed and substantially parallel and proximally spaced so that the liquid wets and spreads upon both surfaces;
an adjustable sample measuring position so selected that the opposed substantially parallel surfaces are spaced apart to pull the sample into a column wherein it is contained by surface tension thereby providing an optical path for a photometric or spectrophotometric measurement.

2. An apparatus as in claim 1 wherein the source is coupled to the sample with an optical fiber or light pipe.

3. An apparatus as in claim 1 wherein the detector is coupled to the sample with an optical fiber or light pipe.

4. An apparatus as in claim 3 wherein the source and detector are each coupled to the sample with an optical fiber or light pipe.

5. An apparatus as in claim 1 wherein there is means such that the optical path between the two surfaces and through the sample can be varied to accommodate a wide range of sample absorbances.

6. An apparatus as in claim 5 wherein the source is intended to excite fluorescence in the sample and the detector has provision to block the source illumination and detect only the fluorescence.

7. An apparatus as in claim 5 wherein the source is coupled to the sample with an optical fiber or light pipe.

8. An apparatus as in claim 5 wherein the detector is coupled to the sample with an optical fiber or light pipe.

9. An apparatus as in claim 5 wherein the optical measurement path can be varied to accommodate variable levels of fluorescence and variable levels of absorbance.

10. An apparatus as in claim 1 wherein the source illuminates the sample from the detection side of the apparatus for the measurement of fluorescence.

11. An apparatus as in claim 10 wherein both the source and the detector are coupled to the sample with an optical fiber or light pipe.

12. Apparatus as in claim 10 wherein the sample optical path can be varied to accommodate variable levels of fluorescence.

13. An apparatus as in claim 1 wherein components of reacting or mixing samples can be applied to each of the two sides allowing photometric measurement to be made as the samples mix or react.

14. A method of using the apparatus of claim 13 wherein components of reacting or mixing samples are applied to each of the two surfaces allowing photometric, spectrophotometric, fluorometric or spectrofluorometric measurement to be made as the samples mix or react.

15. An apparatus as in claim 1 wherein the sample is confined between two thin transparent sheets to prevent contamination or damage to the photometric measurement apparatus or operator.

16. A method of using the apparatus of claim 1 wherein photometric or spectrophotometric measurement is made using two optical pathlengths.

17. An apparatus for performing optical measurements on microliter or sub-microliter liquid samples comprising a frame, a fixed surface or anvil mounted on the frame, a moveable surface or anvil mounted to the frame in substantial parallel opposition to the fixed anvil surface in at least one position, at least two optical fibers penetrating at least one of the surfaces, each of the fibers finished flush with its respective surface, means to move the moveable anvil surface to at least one controlled spacing from the fixed surface and means to perform an optical measurement of the properties of the microliter or sub-microliter liquid sample disposed between the surfaces employing at least one fiber to deliver light to the sample and at least one other fiber to transmit transmitted or excited energy to a detector.

18. The apparatus of claim 17 wherein at least two optical fibers are opposed and each surface is penetrated by at least one fiber.

19. The apparatus of claim 18 wherein the moveable surface is mounted on a swing arm pivotally related to the fixed surface.

20. The apparatus of claim 19 wherein the moveable surface and swing arm are disposed to be manually pivoted to rest upon on of the two tips of the plunger of a solenoid fixedly mounted to the fixed surface and the other tip of the plunger is biased toward the moveable surface so that the swing arm can be manually depressed to compress the sample between the two surfaces, or the solenoid can be energized to compress the sample, whereby the sample wets both surfaces, but when the solenoid is not energized and no manual force is applied to the swing arm the two surfaces are spaced a selected distance apart to provide a desired optical path through the sample for measurement.

21. The apparatus of claim 20 wherein an adjustable stop regulates the spacing between the two surfaces when the solenoid plunger is depressed.

22. The apparatus of claim 21 wherein a permanent magnet mounted on the swing arm interacts with the framw to hold the swing arm in either the open or closed position.

23. An apparatus wherein the sample is contained in a small vessel with flexible walls such that the sample can be pulled into a measurement column between the fixed and moveable anvil surfaces and its absorbance measured as a difference in absorbance between two optical pathlengths.

24. A method of using the apparatus of claim 23 wherein the sample is enclosed in the small vessel with flexible walls, the surfaces of the apparatus are wetted, the vessel is placed between the surfaces of the apparatus and the sample is pulled into a measurement column by separating the surfaces while the sample absorbance is measured as a difference in absorbance between paths of two pathlengths.

25. In apparatus for the photometric or spectrophotometric measurement of small liquid volume samples the improvement comprising holding the sample by surface tension between two surfaces, adjusting the distance between those two surfaces such that the sample is drawn into a column by separating the two surfaces to a selected measuring distance, and performing the measurement employing a photometric or spectrophotometric detector each in one of the surfaces.

26. The apparatus of claim 25 wherein the source is coupled to the sample with an optical fiber or light pipe.

27. The apparatus of claim 25 wherein the detector is couples to the sample with an optical fiber or light pipe.

28. The apparatus of claim 27 wherein the optical path is established through the sample between the source and detector and this path can be varied by adjusting the distance between the two surfaces.

29. A method of performing a photometric or spectrophotometric measurement on a microdrop liquid sample comprising: placing the sample on one of two relatively moveable opposing surfaces, or placing a part of the sample on each sutrface; moving the surfaces toward each other a preselecv6ed distance to spread the sample and to wet the surfaces; moving the surfaces apart from each other a preselected distance whereby the sample is contained between tuhe surfaces by surface tension; and performing the photometric or spectrophotometric measurement.

30. Apparatus for performing a plurality of optical measurements simultaneously on microliter or sub-microliter samples Comprising an equal plurality of the apparatus of claim 17 assembled in unitary form.

* * * * *